ized Immunosorbent

United States Patent [19]

Lopez et al.

[11] Patent Number: 5,183,735
[45] Date of Patent: Feb. 2, 1993

[54] METHOD AND DIAGNOSTIC TEST KIT FOR DETECTION OF ANTI-DSDNA ANTIBODIES

[75] Inventors: Luis R. Lopez, Aurora; Marcia Sterhan, Louisville, both of Colo.

[73] Assignee: Reaads Medical Products, Inc., Westminster, Colo.

[21] Appl. No.: 633,361

[22] Filed: Dec. 27, 1990

Related U.S. Application Data

[63] Continuation-in-part of Ser. No. 315,567, Feb. 27, 1989.

[51] Int. Cl.$^5$ .............................................. C12Q 1/68
[52] U.S. Cl. .......................................... 435/6; 435/7.1; 435/7.5; 435/7.9; 435/7.92; 435/975; 422/56; 422/61
[58] Field of Search ................. 435/6, 7.1, 7.5, 7.9, 435/7.92, 975; 422/56, 61

[56] References Cited

PUBLICATIONS

Rubin et al: An Improved ELISA . . . Antibodies J. Immunol. Methods 63; pp. 359–366 (1983).
Vogt et al., J. Immunol. Methods 101 pp. 43–50 (1987).
*Journal of Immunological Methods*, vol. 101 issued 1987, R. F. Vogt, Jr. et al., "Quantitative differences among various proteins as blocking agents for ELISA microtiter plates", 43–50.
*Clinical and Experimental Rheumatology*, vol. 5, issued 1987, A. G. Tzioufas, et al., "Enzyme immunoassays for the detection of IgG and IGM anti-ds DNA antibodies: clinical significance and specificity", 247–253.
*Journal of immunological Methods*, vol. 48, issued 1987, Valesini et al., "The Trypanosoma Lewisi Immunoflorescense Test: A New Simple Technique for Simultaneous Determination of Total Antinuclear Antibodies and the Detection of Antibodies to double-stranded DNA" 177–188.
*Journal of immunological methods*, vol. 85, Issued 1985, Kenna et al., "Methods for Reducing Non-specific Antibody Binding in Enzyme-linked Immunosorbent Assays" 409–419.

*Primary Examiner*—Christine M. Nucker
*Assistant Examiner*—Jeffrey Stucker

[57] ABSTRACT

A diagnostic element for detecting the presence of anti-dsDNA antibodies in a sample. The diagnostic element includes a support (e.g., a microcell), a coating of mBSA on the support, dsDNA antigens immobilized on the coating, and a blocking layer for blocking immobilization sites other than ones occupied by dsDNA antigens. A testing kit is also provided which includes a diagnostic element, a sample diluent, an antibody solution, and a label identifying solution.

13 Claims, 5 Drawing Sheets

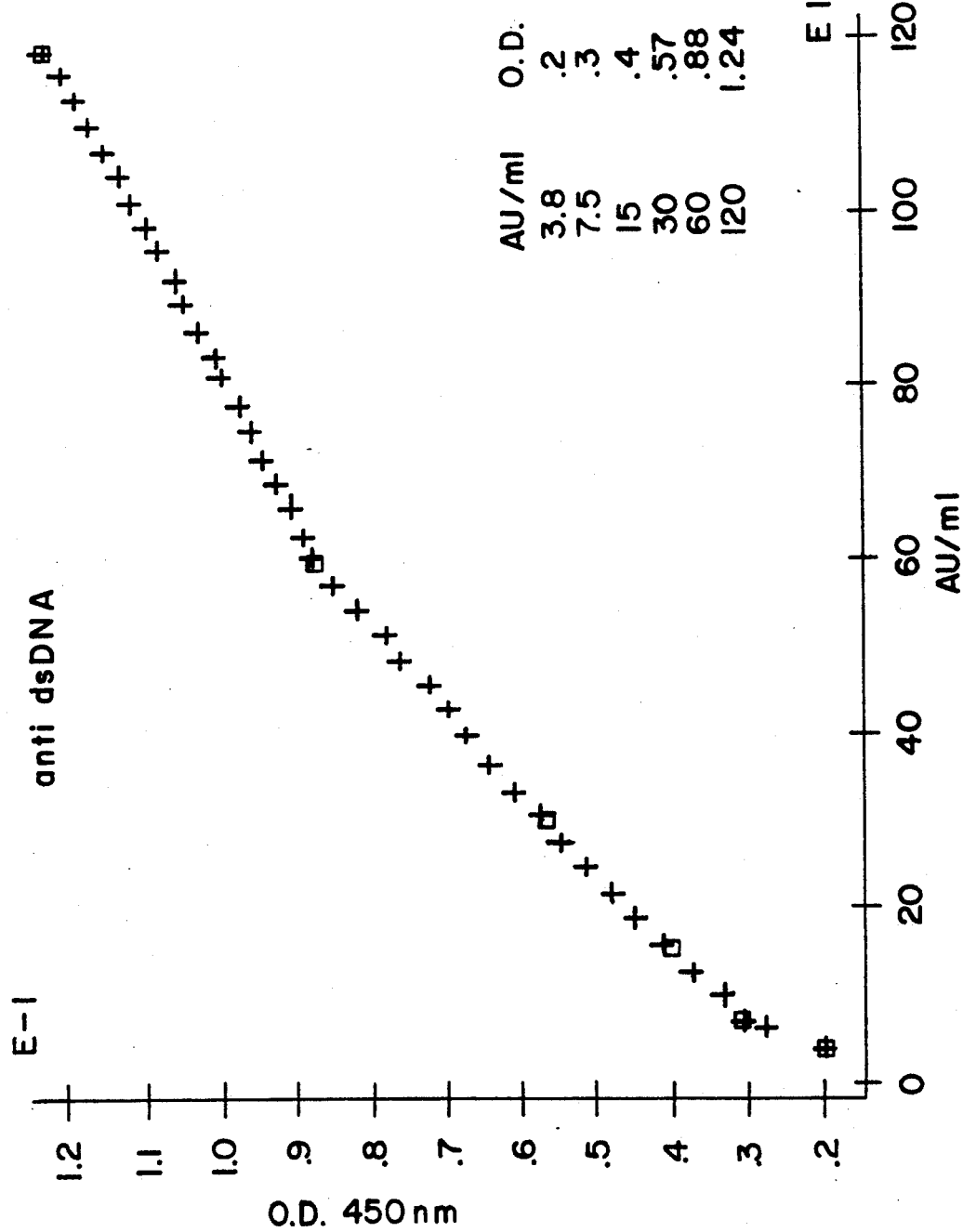

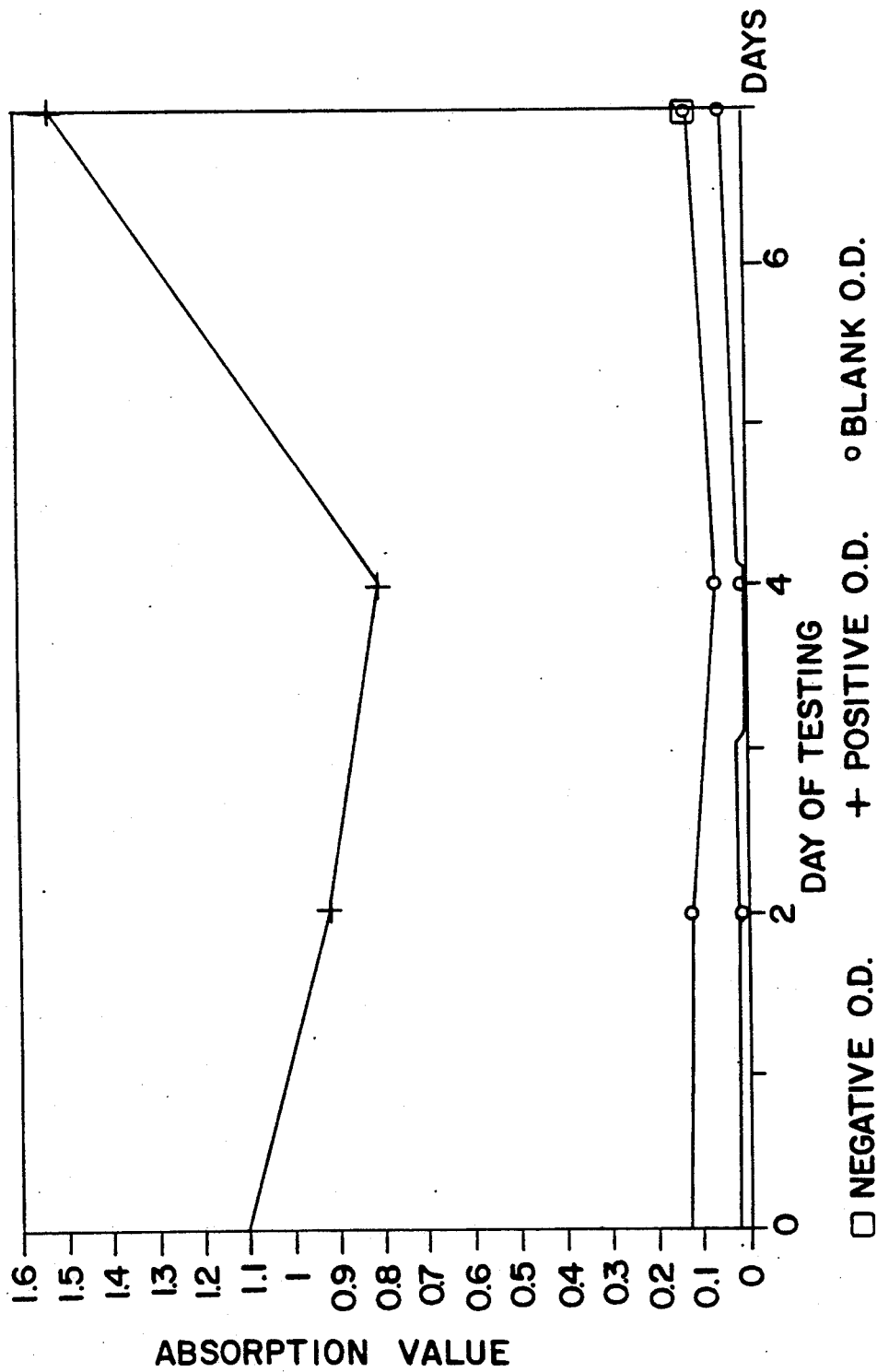

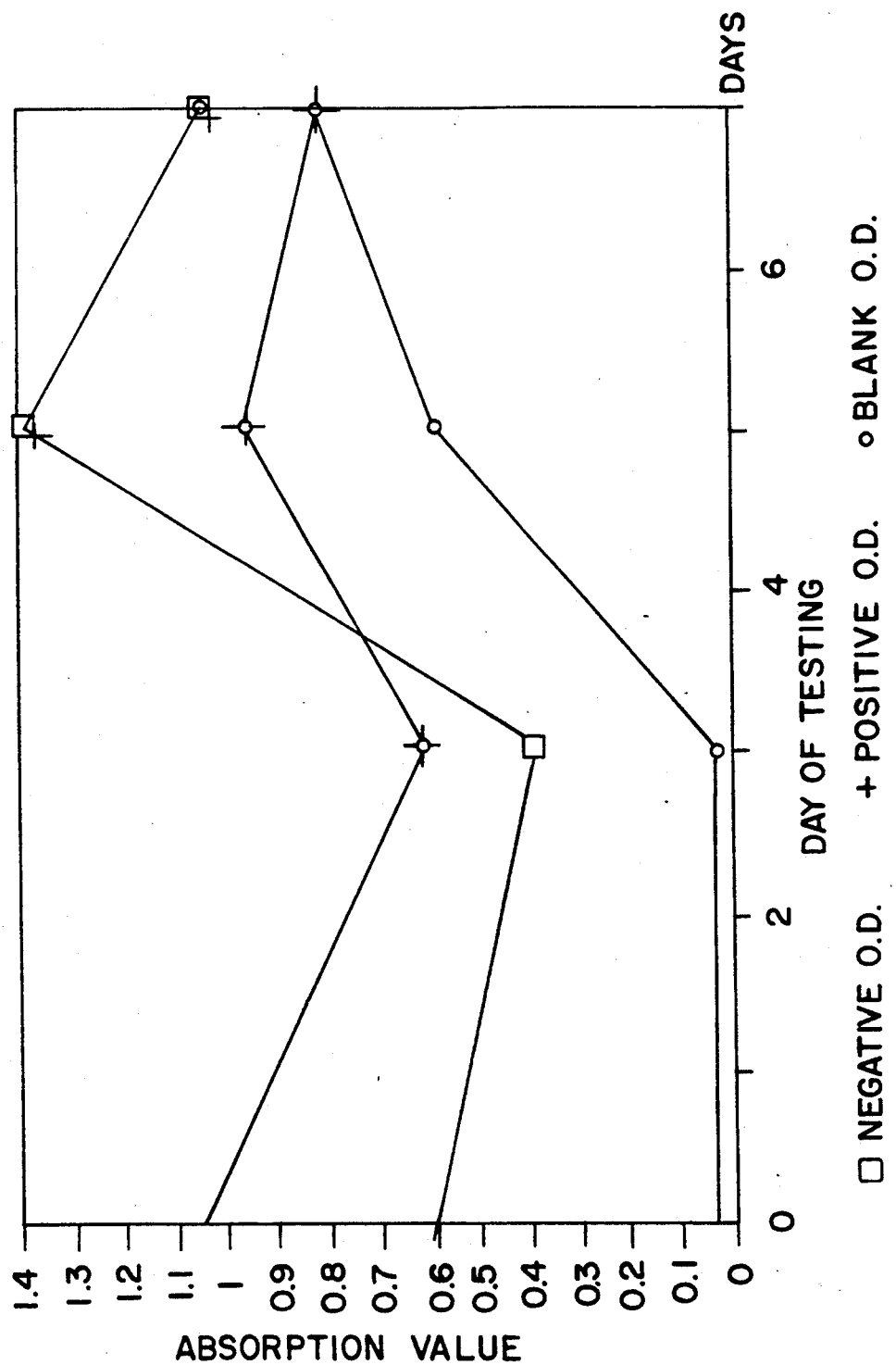

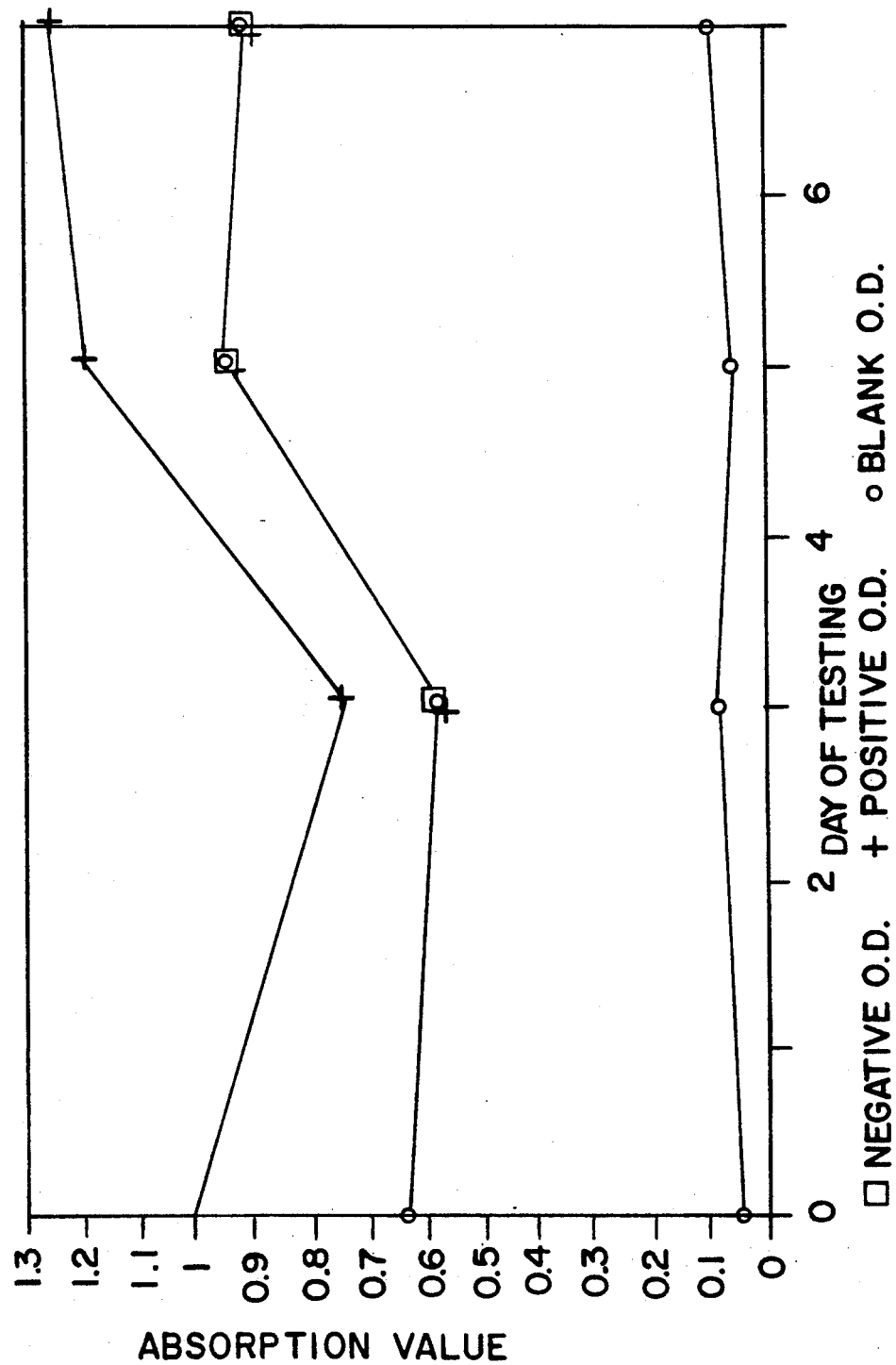

METHOD AND DIAGNOSTIC TEST KIT FOR DETECTION OF ANTI-DSDNA ANTIBODIES

RELATED APPLICATION

This application is a continuation-in-part of our pending U.S. patent application Ser. No. 315,567 filed Feb. 27, 1989.

BACKGROUND OF THE INVENTION

The immune system is the body's defense mechanism against foreign substances and invading microorganisms. The underlying operating principle of the immune system is a self/non-self recognition pattern. If the invader organism is recognized as not being part of the "self", then a defensive immune response is mounted against it. In the case of autoimmune diseases, the immune system fails to properly recognize "self" and mounts a defense immune response against its own normal body components.

Antibodies generated by the immune system to diverse tissue and cellular components have been used to diagnose and monitor autoimmune disease activity. In systemic lupus erythematosus (SLE) (a type of autoimmune disease) one of the antibodies produced reacts with DNA that is found widely distributed in cell nuclei in a multitude of body tissues. Formation of antibodies to double-stranded or native deoxyribonucleic acid (anti-dsDNA), is relatively specific to SLE. Although other disorders, such as Mixed Connective Tissue Disease (MCTD), drug induced lupus (DIL), Rheumatoid Arthritis, Scleroderma, and Sjorgren Syndrome, produce similar clinical manifestations as SLE, high levels of anti-dsDNA are seldom associated with these disorders. Therefore, detecting anti-dsDNA is useful in specifically diagnosing SLE. Anti-dsDNA levels correlate well with the disease activity of the patient; thus making it a good monitoring tool.

Many different techniques and different diagnostic kits have been developed in the search for a standardized, accurate, rapid, and stable method for the detection of anti-dsDNA. Most of the methods have been somewhat successful, but due to unacceptably high levels of cross-reactivity (such as with single-stranded DNA [ssDNA]), the slow run time of the assays, and the short shelf life of the kit components, no method is fully adequate. Examples of the limitations of the prior methods follow.

A number of techniques have been developed to detect antibodies to dsDNA, including immunofluorescent assays (FIA), radioimmunoassay (RIA), and enzyme-linked immunosorbent assays (ELISA).

Firstly, the RIA technique has been developed in a variety of formats to measure levels of anti-dsDNA in sera. A RIA diagnostic test kit (using the Farr technique) has been developed by Diagnostic Products, Inc. for commercial sale to clinical laboratories. This test precipitates the bound labeled DNA which is then retained for counting. This test is sensitive to high levels of anti-dsDNA but has less specificity in lower levels of anti-dsDNA activity, thus resulting in false negatives. Unfortunately, this test has a run time of approximately two hours and fifteen minutes, and a limited stable shelf life. Furthermore, this test kit has the same draw-backs which are inherent in all RIAs; the expense associated with radioactive material, which also has a limited shelf life and can be potentially dangerous.

Secondly, Crithidia luciliae immunofluorescence tests have been developed as diagnostic test kits for the detection of anti-dsDNA. This test kit is based on a staining method associated with the kinetoplast of the protozoan. A positive reaction is demonstrated by detection of specific fluorescence in the kinetoplast of most cells. The kinetoplast, within the protozoan, contains many other components besides dsDNA which can cross react with anti-dsDNA or other antibodies, thus rendering false positive results. This test is extremely subjective, as it is based on an individual's ability to recognize a positive fluorescent pattern. Furthermore, this method, which has a run time of approximately two hours, has a lack of sensitivity in low levels of concentration of anti-dsDNA resulting in false negatives. The false negative and false positive results make this method more useful when used together with other tests in clinical practice.

Thirdly, the immunological community has developed diagnostic test kits for the determination of anti-dsDNA levels in the standard ELISA format. Although a variety of these kits have been developed, the same limitations of stability, cross reactivity with ssDNA, and length of run time plague each assay. Many of these kits claim a low level of cross reactivity with ssDNA which should render good sensitivity to low, medium, and high levels of anti-dsDNA; however, as evidenced by the kit instructions, the test shows a lack of sensitivity to the sera sample which are borderline positives. As a consequence, these kits cannot be used to accurately monitor patients who are borderline positives. In fact, most kits require that low positives must be retested to assure confidence in the results, thereby increasing the cost to the patient. Development of an assay which is sensitive to all levels of anti-dsDNA can only be achieved by reducing non-specific binding by such components as ssDNA.

R. Rubin, An Improved ELISA for Anti-Native DNA by Elimination of Interference by Anti-Histone Antibodies; J. Immunol, Methods, at 359 (1983) discusses an enzyme linked immunosorbentassay for antibodies to native DNA in which methylated bovine serum albumin (mBSA) was used to link DNA antigen (which had undergone digestion with $S_1$ nuclease to polystyrene. After immobilizing DNA to the kit a gelatin was incubated in the wells to avoid problems with nonspecific binding. Thereafter, the microwells could be stored until use, however, prior to use the immobilized DNA in the wells must be re-digested with $S_1$ nuclease.

The final additional step requiring $S_1$ nuclease re-digestion prior to use of the plate suggests that the ssDNA present in stored microtiter plates has reached an unacceptable level and the kit lacks stability.

The Rubin coating method was compared with the present invention and the results showed that the present invention has significantly better stability, specificity and sensitivity than this kit. Factors that may contribute to the results obtained by the present invention includes the order in which the plates are coated, the blocker used and the solution the blocking agent is placed in, the lack of Tween 20, the incubation times and temperatures employed for the various coating step.

Specifically, addressing some of the above listed factors it is believed that coating the blocker after the immobilized dsDNA is treated with $S_1$ nuclease permits less nonspecific binding than does coating the blocker prior to treating the dsDNA with S₁ nuclease, because the treatment of S₁ nuclease can lead to open binding sites on the support which are not blocked. Furthermore, the gelatin blocker used by Rubin is not believed to block as efficiently as a casein blocker used in the present invention.

Combining the teachings of Rubin's precoating method above with a casein blocker, the use of casein as a general blocking agent is suggested in an article by Robert F. Vogt et al, 1987 J. Immunol. Methods 101, 43 still resulted in significantly lower stability, specificity and sensitivity results than the results obtained by the present invention. Again, the similar factors are believed to contribute to these results. Specifically, the solution that the blocker is placed in in the present invention is adapted to smoothly coat the wells uniformly and also may increase the stability of the pre-coated wells, unlike the blocker material suggested by Vogt. Furthermore, in development of the present invention, certain experimental results may suggest that using Tween 20 may adversely effect the test kit results and thus unlike the Rubin and Rubin-Vogt pre-coating procedures, Tween 20 is not employed in the present invention.

Furthermore, performance of an assay on serum suspected of containing anti-dsDNA antibodies can be performed in less then one hour and forty-five minutes which is significantly less time than required by the Rubin protocol.

BRIEF SUMMARY OF THE INVENTION

An object of this invention is to have a test kit that detects anti-dsDNA antibodies that shows a negligible absorbance of a reagent blank and an absorbance ratio of a negative control/positive control that is at least 1.7 and preferably greater than 5.0 throughout a week long accelerated stability test.

An object of this invention is to have a test kit that shows specificity of over 62% and preferably shows specificity between 80%-100%.

A still further object of this invention is to have a test kit that has low levels of cross reactivity.

Also another object of this invention is to have an assay that has a run time of less then one hour and forty-five minutes and preferably having a run time of one hour or less.

Also another object of this invention is to have a test kit that produces less then 6% ssDNA activity in thirteen days or the equivalent of 19.5 months in accelerated stability studies.

A further object of this test kit is to have a coating order and procedure which eliminates much of the non-specific binding problems evidenced by low specificity.

It is therefore an objective of the present invention to provide compositions, methods, articles, and a diagnostic test kit for the selective adsorption, or affixing of dsDNA antigen to a pre-coated plate for the effective detection of anti-dsDNA antibodies present in a sample specimen such as sera or plasma or other bodily fluids. It is a further objective of this invention to overcome the aforementioned specificity sensitivity, stability, run time and shelf life disadvantages inherent in many of the previously described assays. It is, moreover, also an objective of this invention to provide in the form of a kit a novel, readily utilizable means for quantitative and qualitative detection of anti-dsDNA antibodies. This will provide a method and apparatus for the purpose of clinical detection of anti-dsDNA, or the detection of anti-dsDNA for any other purpose associated with human or animal medical testing.

The present invention includes novel compositions, novel methods and articles for the direct selective absorption, adsorption or attachment, by whatever mechanism, of the anti-dsDNA from the body fluid sample to the dsDNA coated onto any suitable solid support, such as test tubes, plates or wells (hereinafter referred to as wells or microwells), for the purpose of quantitative and qualitative identification. The present invention utilizes immobilized native DNA from whatever source, which has an affinity for attachment of anti-dsDNA.

This invention utilizes a sandwich ELISA format which includes pre-coated wells made of any suitable material such as plastic, glass, etc., and the various reagents and antibodies necessary to run a highly sensitive, 45-35 minute assay for the presence of anti-dsDNA.

The various reagents and the method of coating these reagents to the microwells have been employed advantageously in the practice of the present invention to formulate a test which has minimized or eliminated the problems associated with previous assays. The coating protocol has advantageously utilized methylated bovine serum albumin (mBSA) for two main purposes; namely, the mBSA provides a positively charged surface which enhances the adherence of the dsDNA to the polystyrene wells, and second to eliminate false positives due to the binding of anti-histone antibodies. The use of mBSA as a coating prior to the application of DNA antigen for use in solid phase assays for anti-dsDNA was explored by R. Rubin (J. Immunology 63, 359-366 [1983]). In the practice of this invention, protamine sulfate as well as other functionally equivalent substitutes have been found to be capable of forming a reactivity charged surface; however, due to the reactivity of these coatings with other components such as ssDNA and anti-histone antibodies, mBSA is preferred. It was highly surprising to find that a coating of mBSA on a solid support underlying the DNA antigen provides the pre-coated wells with a consistently high level of reproducibility even over a period of one year.

Methylated Bovine Serum Albumin is utilized for the previously mentioned reasons, the second of which is directly related to the specificity and sensitivity of this assay. The lack of good correlation between ELISAs, RIAs and Crithidia luciliae staining procedures in some cases appears to be due to binding by anti-histone antibodies which gives the ELISA an elevated anti-dsDNA reading. The mBSA pre-coating appears to have alleviated this area of non-specific binding.

A second factor which contributes to the lack of sensitivity and non-specificity is the cross reactivity between ssDNA antigens and anti-dsDNA antibodies. To eliminate the potential binding of the anti-dsDNA antibodies to ssDNA antigens the microwells which have been coated with dsDNA were treated with an endonuclease, S₁ nuclease, which is an enzyme specific for the breakdown degradation of ssDNA and has no affect on dsDNA. Although other anti-dsDNA tests utilize S₁ nuclease (for example see A. G. Tzioufas, Clinical and Experimental Rheumatology 5, 247-253 [1987]) their sensitivity levels are still substantially lower than acceptable levels for patients with borderline positives. The use of S₁ nuclease in a digestion buffer with an acid pH on the immobilized dsDNA antigens, combined with the use of a mBSA pre-coating substantially eliminates ssDNA activity and anti-histone activity providing a highly sensitive and specific assay which renders few false positives.

The shelf life and the reproducibility of results from the ELISA is associated not only with the mBSA pre-coating, and the $S_1$ nuclease treatment and the order of the coating procedure, but also with the next two steps of forming the pre-treated wells; and the addition of a hydrolyzed casein blocker and the drying.

A casein-type blocker has been used in various ELISA techniques (Robert F. Vogt, J. Immunological Methods, 101, 43-50 [1987]) to block non-specific binding to plastic through a protein-plastic interaction. It is an unexpected realization that a coating of hydrolyzed casein blocker maintained a consistent inhibition of non-specific binding over an extended period of time, when the wells were stored at 4 degrees C in a sealed plastic bag.

Although the direct mechanisms by which the drying process and the blocker increases the stability and shelf life of the wells is not fully understood, it is obvious that the storage time is increased by these processes. Little to no ssDNA is generated during the storage conditions by this method in a period of up to one year.

A variety of differing block agents could be utilized which are functionally equivalent to or chemically related to the casein blocking agent. For example, BSA and porcine thyroglobulin, dried milk, whole goat serum, etc., however the most preferable is the hydrolyzed casein (commercially available from Sigma) due to its high level of inhibition of non-specific binding and its storage stability.

This invention's method utilizing mBSA, the $S_1$ nuclease treatment, combined with the casein blocker and the blocker solution and the drying process have unexpectedly resulted in a novel assay which is characterized by a low level of cross-reactivity with ssDNA, a high level of inhibition of non-specific binding, and a long shelf life. Particularly, non-specific binding is reduced so that the diagnostic element has a specificity greater than sixty-two percent, but preferably greater than ninety percent.

The pre-coated wells are then used to detect the presence of anti-dsDNA antibody in the sample. The plasma or serum samples are prepared with a sample diluent and are then assayed for their components by an immunoassay technique, the ELISA and the fluorescent immunoassay (FIA) formats being the preferred methods, though it is possible to perform a RIA or a luminescent assay with little modification.

The assays depicted in the following examples have a preferable run time of 45 minutes or less, but at least within 105 minutes after contact with a sample specimen. The wells, when exposed to the samples, are provided with approximately 15 minutes at room temperature to allow the binding of the anti-dsDNA to the dsDNA to go to completion. Then the labeled goat anti-human antibodies are exposed to the wells and a similar 15 minute incubation at room temperature is provided for. If the enzyme is utilized then a substrate can be added (although this is not necessary) and 10 minutes is allotted for the production of the color. If a fluorescent marker is used on the goat anti-human antibody then no substrate is needed, therefore the run time is shortened by 10 minutes reducing it to 35 minutes.

Subsequent qualitative and quantitative detection of the anti-dsDNA antibody is relatively simple if the format is either an ELISA or a FIA. Numerous enzyme-conjugated antibodies and fluorescent-labeled antibodies specific for any of the immunoglobulin classes can be utilized in this invention. The quantitation of the anti-dsDNA antibodies present is accomplished by the related instruments. The ELISA technique utilizes a spectrophotometer, and the FIA technique utilizes a microfluorometer. Use of the ELISA techniques were first described by Engvall and Perlman ([1971] Immunochemistry 8, 871-874 and [1972] J. Immunology 109, 129-135), and The Enzyme Linked Immunosorbent Assay (ELISA) by Voller, A., Bidwell, D. E., and Bartlett, A., (1979) Dynatech Laboratories, Inc., Alexandria, Va., both of which are, in their totality, incorporated herein by reference.

According to the present invention, then, a diagnostic element is provided with this diagnostic element being adapted to detect the presence of anti-dsDNA antibodies in a sample specimen upon contact. In this broad form, this diagnostic element includes a support member which has a coating on a surface portion thereof. The coating includes a methylated bovine serum albumin as a constituent thereof in order to provide immobilization sites for dsDNA antigens. The dsDNA antigens are then attached at selected one of the immobilization sites to define occupied immobilization sites. A blocking layer is then disposed on the coating with this blocking layer including a blocking material that is operative to block a majority of the immobilization sites other than the occupied sites. The blocking layer thus provides a contact surface available to be contacted by the sample specimen. This contact surface has dsDNA antigens which form binding sites specific for the anti-dsDNA antibodies, if any, present in the sample specimen. At the same time, the contact surface is substantially free of ssDNA antigens which would otherwise form binding sites. The blocking material may include casein and, if desired, the blocking material may also include glycerol and sucrose. In particular, the blocking layer is operative to stabilize the dsDNA antigens which are immobilized on the occupied ones of the immobilization sites so that the contact surface has a specificity greater than 62%, and preferably 90%.

The diagnostic element may be used to provide a test kit which includes not only the diagnostic element, as constructed above, but also a sample diluent which may be used to dilute the sample specimen prior to application thereof to the contact surface. The kit may also include a conjugated antibody solution which has anti-human IgM and IgG antibodies conjugated to a label and operative to become affixed to bound ones of said anti-dsDNA specific antibodies upon contact therewith. Thus, the relative amount of anti-dsDNA specific antibodies in the sample specimen can be determined by various measuring techniques. To this end, the diagnostic test kit may also include a label identifying solution operative to permit analyzation of attached conjugated antibody solution labels. Preferably, the sample diluent includes a native bovine serum which is operative to inhibit the binding of non-specific antibodies to said coating.

The methodologies according to the present invention include a method of producing a diagnostic element as well as a method for detecting the presence of anti-dsDNA antibody in a sample specimen. The method producing a diagnostic element includes a first step of providing a support, and this support is coated along a surface portion with a first substance which includes methylated bovine serum albumin to form a layer having immobilization sites. Next, the layer is contacted with dsDNA antigens which are specific for the anti-dsDNA antibodies in order that at least some of the dsDNA antigens attach to the methylated bovine serum albumin at some of the immobilization sites. After the layer is so contacted, it is washed with a second substance which includes an enzyme capable of digesting ssDNA. Finally, the first layer is coated with a third substance that includes a blocking material operative to eliminate available ones of the immobilization sites and to stabilize the dsDNA antigens.

The methodology of producing the diagnostic element preferably utilizes a second substance which includes an $S_1$ nuclease digestion buffer operative to eliminate ssDNA. Further, it is preferred that the step of contacting the first layer with dsDNA antigens and the step of coating the first layer with a third substance produces a ratio specific to non-specific binding sites such that the amount of specific binding produced by contact of the contact surface with a positive control to the amount of non-specific binding produced by contact of said contact surface with a negative control is at least 1.7 to 1, but preferably 5 to 1.

While the present invention is directed to a method of detecting the presence of anti-dsDNA antibody in a sample specimen, the processing steps include the first step of providing a diagnostic element in the form of a support member generally described above after which the contact surface of the diagnostic element is contacted with said sample specimen. Next, the contact surface is contacted with a labeled antibody whereby at least some of the labeled antibody binds as a bound label to said anti-dsDNA antibody. The contact surface is then rinsed after contact thereof with the labeled antibody. The final step of the broad method, then, contemplates measuring the amount of the bound label material within 105 minutes after contact of the contact surface with the sample specimen in order to determine the amount of anti-dsDNA antibody which is present. In the preferred methodology, the step of contacting the contact surface of the labeled antibody occurs within 15 minutes after the step of contacting the contact surface with the sample specimen. Finally, the step of measuring the amount of bound label is done within a preferable time of 45 minutes or less after contact of the contact surface with the sample specimen.

These and other objects of the present invention will become more readily appreciated and understood from a consideration of the following detailed description of the preferred embodiment when taken together with the accompanying drawings, in which:

BRIEF DESCRIPTION OF THE FIGURES

FIG. 2—This graph depicts a standardized curve obtained from the data obtained in Example 3;

FIG. 3 shows the absorbance of a negative dsDNA control serum, a reagent blank and a positive dsDNA control in an accelerated stability study using a test kit coated in accordance with the present invention;

FIG. 4 shows the absorbance of a negative dsDNA control serum, a reagent blank and a positive dsDNA control in an accelerated stability study using a test kit coated in accordance with the Rubin Method; and FIG. 5 shows the absorbance of a negative dsDNA control serum, a reagent blank and a positive dsDNA control in an accelerated stability study using a test kit in accordance with the Rubin and Vogt Method.

DETAILED DESCRIPTION OF THE INVENTION

Figure 1:
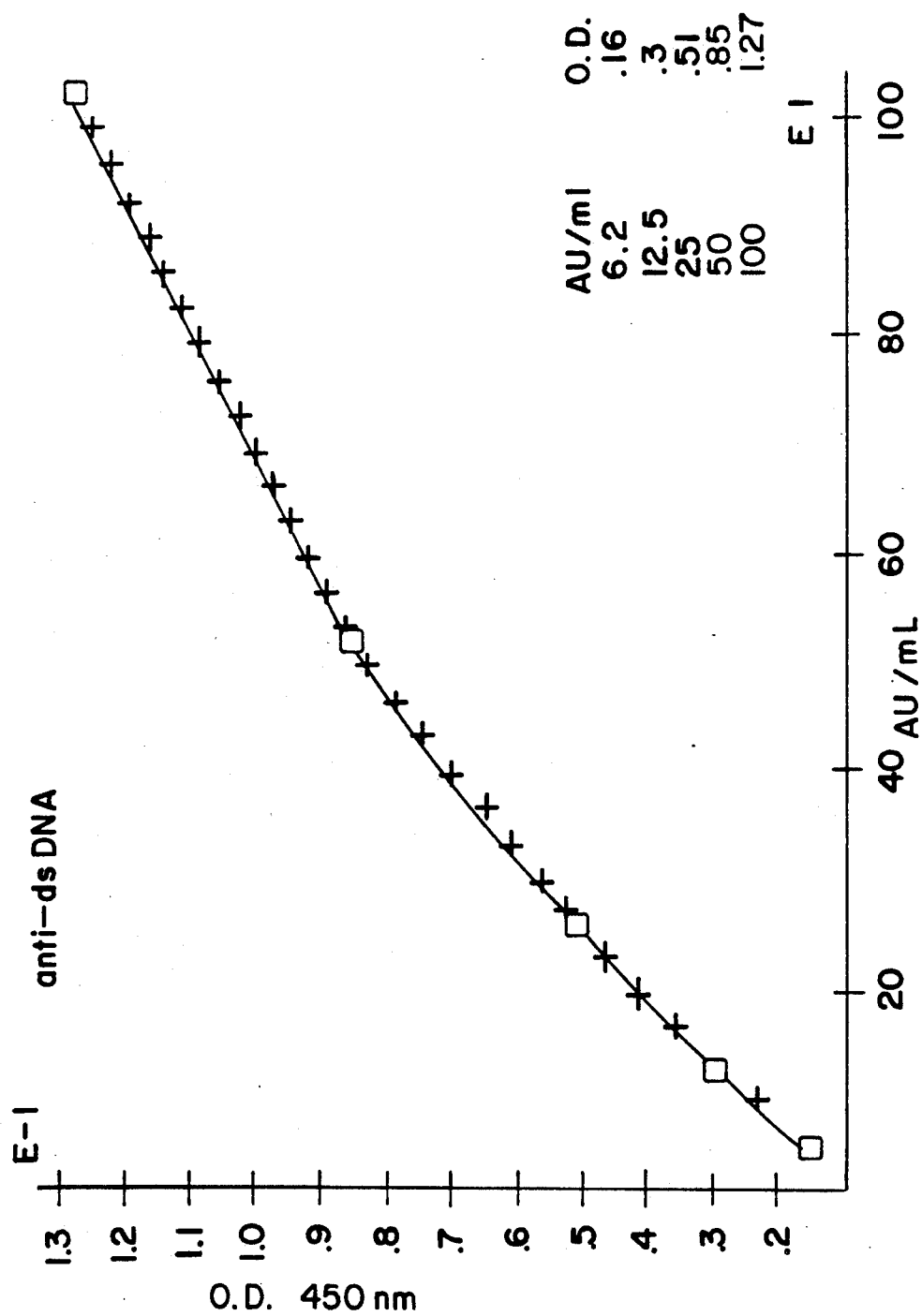
FIG. 1—This graph depicts a standardized curve based on arbitrary units/ml vs. O.D. 450 nm. This curve was generated by using the ELISA format of this invention. The Center for Disease Control (CDC) ANA Human Reference Serum #1 has an antigen binding capacity of 0.59 micro grams DNA bound per ml of serum. This is equivalent to 100 AU per ml.

The following definitions are supplied for the purpose of clarifying the invention and are not intended to limit the scope of the invention:

Methylated Bovine Serum Albumin Solution: Unless otherwise specified, is intended to mean a solution of 1 milliliter of water or PBS with 20 micrograms of methylated bovine serum albumin (mBSA) dissolved in it. A substitute for mBSA is protamine sulfate or any other chemical or chemical process capable of producing a slightly positively charged coating which is evenly distributed over the surface of the microtitre well.

PBS Solution: A 0.01 molar solution of buffer containing 1.43 g potassium phosphate, dibasic, 0.25 g potassium phosphate, monobasic, and 8.5 g sodium chloride in one liter of water. The pH is $7.3+/-0.1$.

dsDNA Solution: Purified dsDNA solution from calf thymus was utilized. Alternative sources of DNA include, but are not limited to, native linear DNA from E. Coli, and circular DNA from plasmid, virus, crithidia, and synthetic polynucleotides (poly (dA.dT)).

Casein Blocker Solution: 15 milligrams of hydrolyzed casein blocker (Sigma), 2 ml glycerol, 10 grams sucrose was dissolved in TEN buffer sufficient to bring the final volume to 100 mls. The solution is adjusted to pH $7.3+/-0.1$.

TEN Buffer: Is made by adding 6.1 g TRIS, 0.38 g EDTA, 8.8 g NaCL, 3.8 mL of concentrated HCL to 900 mL deionized water. Adjust pH to 7.3 and add deionized water sufficient to give 1000 milliliter total volume.

Anti-dsDNA Antibody: Circulating autoantibodies directed against dsDNA.

$S_1$ Nuclease: An endonuclease (enzyme) which is capable of digestion of ssDNA antigen.

Double Antibody Sandwich ELISA or FIA: A solid support is coated with material which detects and binds the antibody of interest to the coated surface. To render a signal, a second conjugated antibody with an affinity for the previously bound antibody is exposed to the coated surface. This antibody binding to the original antibody makes the sandwich. If the sandwich assay is an ELISA then the second antibody is conjugated with an enzyme and substrate is used to produce a color. If the assay is an FIA then the second antibody is marked with a fluorescent tag and a substrate is unnecessary.

Buffer for $S_1$ Nuclease Digestion: 95 mls of acetate/acetic acid buffer, pH 4.6, is mixed with 5 mls glycerol, 0.29 g NaCL, 0.029 g $ZnSO_4$, for a final volume of 100 mls.

$S_1$ Nuclease Buffer Solution: Buffer for $S_1$ nuclease digestion plus 100 units (Sigma) $S_1$ nuclease per ml of buffer. One unit of $S_1$ nuclease is defined as: Causing 1.0 microgram of ssDNA per minute to become perchloric acid soluble at pH 4.6 and 37 degrees C.

Serum: Is intended to mean the fluid component of any body fluid remaining after cells and coagulable proteins such as fibrin which may be present in such body fluidic components have been removed by appropriate physical, chemical or physicochemical mean.

Typically, this term refers to the residual watery fluid remaining after clotting of blood and removal of the clot, but in its broad sense is intended to include the fluidic component of cerebrospinal fluid, urine, interstitial fluid, cellular cytoplasm, and the like.

Sample Diluent: A 1 liter solution has 100 mls of native bovine serum, 1.42 grams of potassium phosphate (dibasic), 0.26 g of potassium phosphate (monobasic), 1 gram of sodium azide, and 8.6 grams of sodium chloride dissolved in 900 mls of water. If an ELISA is run, then 1 ml of stock green dye is added to the solution. If the FIA format is used then the dye is unnecessary. The solution is then filtered through a 0.2 micron filter and stored at 4 degrees C.

Diluted Sample Solution: 10 microliters of sera dissolved in 500 microliter of sample diluent.

Conjugate Diluent: A phosphate buffer, and protein stabilizer, plus 0.02% thimerosal adjusted to a pH of 7.5 (commercially available from Medix Biotech Inc.) into which is added a protease inhibitor, aprotinin, (commercially available from Miles Pentex) at 0.01% of the volume of the buffer.

Working Conjugated Antibody Solution: 1 volume of concentrated conjugated antibodies/3000 volumes of conjugated diluent. The dilution is subject to change based on the concentration level of the conjugated antibody.

Conjugated Antibodies: For an ELISA, antibodies were chemically conjugated with horseradish peroxidase. For FIA, antibodies were chemically conjugated with Fluorescein Isothiocyanate.

Immunoglobulin: Any member of the gammaglobulin fraction of serum possessing the ability to bind another agent.

Antigen: Molecules (from whatever source, nature or man-made) which induce an immune reaction when recognized by the host's immune system.

Antibody: A class of serum proteins which specifically bind to an antigen which induced the formation of the antibody.

Immunoglobulin Classes: Antibodies separated by electrophorectic mobility specifically, IgG and IgM.

Substrate Solution: To quantitate the horseradish peroxidase, 100 microliter of buffered (3,3',5,5') Tetramethylbenzidine/hydrogen peroxide (commercially available from Kirkegaard Perry) was used.

Labeled Antibodies: Any antibody substance which has been covalently or otherwise combined with a molecule or ion for the purpose of selectively identifying that group of antibodies. Such adduct molecules or ions include enzymes, fluorescent substances, radionuclides, and the like.

Labeled Antigens: Any antigen substance which has been covalently or otherwise combined with a molecule or ion for the purpose of selectively identifying that group of antigens. Such adduct molecules or ions include enzymes, fluorescent substances, radionuclides, and the like.

Optical Density (OD) or Absorbance: A number which refers to the color absorbance of a sample. Optical density is related to the percent of light transmitted through the sample by the following formula: OD=2-log(percent transmittance).

The preferred embodiment of the method and apparatus for the detection of anti-dsDNA antibodies in sera is a diagnostic test kit. The optimized kit contains:

5 vials (200 microliters) Assay Calibrators for anti-DNA containing these levels of anti-dsDNA activity: 120, 60, 30, 15, 7.5, 3.8 A.U./ml. (quantitative format only);

1 vial (30 ml) Sample Diluent—green solution: contains 0.1% sodium azide;

1 vial Human Negative Serum Control (about 3 A.U./ml);

1 vial High Human Serum Positive Controls—about 100 A.U./ml with antigen binding capacity of $59 \times 10^{-4}$ microgram of DNA;

1 vial Moderate Human Serum Positive Control—about 45 A.U./ml;

12 coated 8-well Microwell Strips with frame holder;

1 vial (15 ml) Conjugated Antibody Working Solution—containing horseradish peroxidase conjugated anti-human IgG, and IgM;

1 bottle (8 ml) TMB Substrate Solution A—contains 3, 3', 5, 5' Tetramethylbenzidine;

1 bottle (8 ml) TMB Substrate Solution B—contains hydrogen peroxide;

1 bottle (12 ml) Stop Reagent: contains 2.5N H2SO4. (1.0N HCL can be used as a substrate);

1 packet Phosphate Buffered Saline (PBS)—reconstitutes to 2 liters of 0.01M PBS, pH 7.4.

Plate Template

This kit for the measurement of anti-dsDNA in serum samples has been designed for use in a clinical laboratory. To determine the AU/ml of the anti-dsDNA present in the sample the kit includes calibrators and controls for generating a standard curve. The selection of the levels of anti-dsDNA activity in these controls and calibrators can be varied without affecting performance of the assay. Optimization of the process has yielded a kit with pre-coated test wells and reagents, which produce low levels of variation between assays and within assays. Furthermore, these reagents and test wells are stable for extended periods of time. This kit has been optimized to have a 45 minute run time at room temperature, which is significantly shorter than other test kits, presently marketed for anti-dsDNA detection.

What follows is a description of a preferred embodiment of the pre-coated wells, and the method of coating the wells of the present invention, along with the preferred method for preparation of and utilization of the various elements of this anti-dsDNA diagnostic test kit.

Step 1: Affixation of the Coating on the Microwells: Methylated Bovine Serum Albumin (mBSA) is dissolved in distilled water or PBS at a ratio of 20 ug/ml. An aliquot of 100 micrograms of this prepared solution is placed in each microwell, to produce a surface which is slightly positively charged. The mBSA serves two important functions; one is to provide a stable evenly coated microwell surface that provides immobilization sites for the antigen, and second is to inhibit non-specific binding such as anti-histone activity. Ten mls of mBSA solution will coat 96 microtiter wells, such as a Dynatech Immulon 2, Dynatech Immulon 4, or Nunc Maxisorp. The coated wells are incubated overnight at 4 degrees C. Unbound mBSA solution is shaken from the wells, and they are rinsed with PBS solution, pH 7.3, and drained thoroughly.

Next, the ligand or antigen is prepared and exposed to the receiving surfaces of the microwells. The antigen attaches to some of the immobilization sites. Purified dsDNA (calf thymus) is dissolved into 0.01M PBS, pH 7.4 in a ratio of 5 micrograms/ml (weight per volume). The buffered ligand is then dispensed into each microwell, 100 microliters of buffered ligand per well.

The binding is enhanced by an incubation period of 18-24 hours at 4 degrees C. The excess solution is shaken from the wells.

The next coating is applied to eliminate the cross reactivity with ssDNA. A buffer is prepared for $S_1$ nuclease digestion. To prepare the buffer 0.03M acetic acid was titrated together with 0.03M sodium acetate in a ratio of 1.1 part acetic acid to 1 part sodium acetate to a final pH of 4.6. 95 mls of the prepared acetate/acetic acid buffer is mixed with 5 mls of glycerol, 0.29 g NaCl, 0.029 g $ZnSO_4$, for a final volume of 100 mls. Added to this buffer was 100 units of $S_1$ nuclease (Sigma) per ml of digestion buffer solution to form a $S_1$ nuclease buffered solution which is dispensed in 100 microliter increments into each individual receiving well. Thus, 10 units of $S_1$ nuclease is contacted with each individual well. This solution is of sufficient concentration to digest the unwanted ssDNA in the previously coated ligand material after a two hour incubation period at 37 degrees C. $S_1$ nuclease eliminates ssDNA which is a source of false positives in many assays. After the incubation period the wells are inverted to remove excess solutions, then the wells are thoroughly rinsed twice with PBS solution. The wells are again inverted on a paper towel and allowed to drain.

The next coating step provides a blocking and stabilizing layer. Here, the microwells of the diagnostic element is contacted with casein blocker (pH of 7.microwells in aliquots of 200 microliters. This step decreases the non-specific binding that can occur due to protein-plastic interaction. The hydrolyzed casein used in the blocker solution can be commercially obtained from Sigma. The casein blocker solution is prepared by mixing 2 ml glycerol, 10 g sucrose, and 15 mg of hydrolyzed casein, and adding sufficient TEN buffer to make 100 ml of solution. This blocking solution is operative to uniformly coat the wells and also possibly to stabilize the coated plates. The wells containing casein blocker solution are again incubated at 4 degrees C. overnight, after which time the wells are inverted and allowed to drain for 15 minutes. Then the wells are uprighted and allowed to dry at room temperature for at least 24 hours.

This completes the process of coating the wells and each diagnostic kit is then supplied with 96 coated wells. The shelf life of coated microwells when stored at 4 degrees C. in a sealed plastic bag is up to one year.

Step 2: Adhering anti-dsDNA to the Prepared Wells From Step 1: The sample diluent is supplied in the kit as a 30 ml green solution. To prepare a 1000 ml solution of Sample Diluent, 100 milliliters of native bovine serum, 1.42 g of Potassium Phosphate (dibasic), 0.26 g of Potassium Phosphate (monobasic), 1 gram of sodium azide, and 8.6 g of sodium chloride, and 1 ml of stock green dye are dissolved in deionized water sufficient to make 1000 milliliters of solution. This solution is then filtered through a 0.2 micron filter.

The Sample Diluent acts as a blocking agent similar to the casein blocker which was previously coated on the wells. The principle blocking component in the Sample Diluent is the native bovine serum which acts to inhibit the binding of any BSA-reactive antibodies to the mBSA coating on the surface of the well.

Prior to contacting the body fluid with the prepared plate, the serum is diluted by adding aliquots of sera to the sample diluent in a 1:50 ratio (volume of serum:-volume of sample diluent), although this exact dilution is not critical and depends upon the nature of the body fluid and the assay techniques employed. To form the diluted sample solution the body fluid is aliquoted in 10 microliter proportions into 500 microliters of Sample Diluent. In an individual well, 100 microliters of the diluted sample is dispensed, and the affixation of the anti-dsDNA is enhances by 15 minutes incubation at room temperature.

Following the affixation of the anti-dsDNA to the coated wells, the wells are thoroughly washed four times with PBS to remove the free unbound antibodies that are present in the sample, which if allowed to remain, would elevate the background absorbance.

Step 3: Assay for the Anti-dsDNA Affixed to the Wells: Standard enzyme-linked immunoassay techniques, previously described, are used for this assay, although any suitable means of detection such as radioactive labeling, fluorescence, or the like can be employed. For the examples described hereinafter, anti-human IgG and anti-human IgM induced in goats were used to ascertain whether anti-dsDNA IgG and IgM antibodies were present. Please note that other species of animal can be used to produce anti-human antibodies. These antisera were linked to horseradish peroxidase, an enzyme which yields a colored product whenever one of its substrates is present together with hydrogen peroxide. The substrate should be chosen to be consistent with the enzyme conjugated to the antibody. For the examples described hereinafter, the substrate was Tetramethylbenzidine and hydrogen peroxide.

The kit contains one 15 ml vial of conjugated antibody solution with anti-human IgM and IgG antibody conjugated to horseradish peroxidase. To prepare a working conjugated antibody solution, a phosphate buffer with protein stabilizer and 0.02% thimerosal solution at pH 7.4 (commercially available from Medix) was mixed with aprotinin, a protease inhibitor (commercially available from Miles Pentex) at a 0.01% ratio of inhibitor to volume of buffer. This diluent enhances the stability of the conjugated antibody. The solution is mixed at a ratio of 1/3000; one part of concentrated conjugated IgM and IgG antibodies is aliquoted into 3000 parts conjugate diluent. The ratio of concentrated conjugated antibody to conjugate diluent is subject to wide latitudes of dilutions based on the manufacturer's concentration of conjugated antibody used in the assay.

Next 100 microliters of the enzyme conjugated goat anti-human antibody working solution, (prepared as described) is added to each microtiter well. Binding of these antibodies to the anti-dsDNA is permitted for at least 15 minutes at room temperature, then the microtiter wells are emptied of their contents, washed four times with PBS, and allowed to drain before the next step.

The presence of a label and antibody, as previously described, is determined by incubating the wells with a solution of buffered (3,3',5,5') Tetramethylbenzidine and hydrogen peroxide. This solution is supplied in the kit in two 8 ml vials; one contains (3,3',5,5') Tetramethylbenzidine; the other vial contains hydrogen peroxide. The separate vials are necessary due to the interaction between the two solution. The two solutions are mixed in a one to one ratio just before use, and 100 microliters of the mixed solution is dispensed into each microwell. The reaction is permitted to continue for 10 minutes at room temperature, or until sufficient color appears to be read on the spectrophotometric device used. The reaction is subsequently stopped through the addition of an equal volume of 2.5 normal sulfuric acid, and the intensity of color (the optical density, "OD", or absorbance) is read by a spectrophotometric device such as a Dynatech MR600 or the like.

As with any enzyme-linked immune assay, the resultant color of the reaction product is proportional to the number of conjugated antibodies which have bound to the anti-dsDNA. For most cases, the number of bound conjugated antibodies is linearly related to the number of anti-dsDNA antibodies. Hence, as the amount of anti-dsDNA bound to the wells increases, so does the optical density, or absorbance of the enzyme reaction.

EXAMPLE 1

Protocol for Pre-coating Microwells with Purified dsDNA

Polystyrene wells were coated with (native) double stranded deoxyribonucleic acid (dsDNA) by the following procedure:

1. Methylated Bovine Serum Albumin (Sigma) (hereinafter designated as mBSA) was dissolved at a ratio of 20 micrograms/ml in distilled water of PBS.

2. 100 microliters of the mBSA solution was placed in each microwell, and incubated overnight at 4 degrees C.

3. The excess coating solution was shaken from the plate after incubation. The plate was rinsed once with a solution of 0.01M PBS, pH 7.3 to remove unbound mBSA. The wells were inverted to drain thoroughly.

4. 5 ug/ml of purified dsDNA was diluted in PBS, 0.01M, pH 7.3, and 100 microliters of the diluted dsDNA solution was dispensed into each microwell and allowed to incubate for 18-24 hours at 4 degrees C.

5. After incubation, the excess dsDNA solution was shaken from the wells and 100 microliters of S-1 nuclease in digestion buffer was added to each well.

6. To form S-1 nuclease buffer solution, 0.03M sodium acetate and 0.03M acetic acid in a 1.1 to 1 ratio at pH 4.6 was prepared. Then 95 mls of this buffer was mixed with 5 mls of glycerol, 0.29 g NaCl and 0.029 g $ZnSO_4$ for a final volume of 100 mls at pH 4.6. S-1 nuclease (Sigma) was dissolved into this solution at a concentration of 100 units/ml buffer. (One unit of S-1 nuclease is defined as causing 1.0 microgram of ssDNA per minute to become perchloric acid soluble at pH 4.6 and 37 degrees C.)

7. 100 microliters of S-1 nuclease buffer solution was contacted with each well for two hours at 37 degrees C. After incubation, the wells were emptied, rinsed twice with PBS, and drained thoroughly.

8. Casein blocker solution (pH 7.3) was dispensed in 200 microliter increments into each well. The casein blocker solution consists of 2 ml glycerol, 10 g sucrose, 15 mg casein and sufficient TEN buffer to bring the volume to 100 ml.

9. The wells coated with the blocker solution were incubated overnight at 4 degrees C. After incubation, the solution was shaken from the wells and the wells were inverted for 15 minutes. Then the wells were uprighted and allowed to dry 24 hours at room temperature.

The coated dsDNA wells were then used to determine the presence of anti-dsDNA in serum samples obtained from individuals with:

1. no apparent pathology (normal);
2. systemic lupus erythematosus.

These sera were drawn from patient with known pathological status. Described hereinafter, is a method of performing an anti-dsDNA assay, using the dsDNA coated wells in a sandwich ELISA format.

1. Standards, sera from patients with no apparent pathology and patients with SLE, a high positive human serum control (100 AU/ml), a moderate positive human serum control (45 AU/ml), and a negative human serum control (3 AU/ml) were diluted with Sample Diluent in a 1:50 ratio; 1 part serum to 50 parts Sample Diluent. The Sample Diluent was a solution consisting of 100 mls of native bovine serum in a phosphate buffered saline consisting of 1.42 g of potassium phosphate (dibasic), 0.26 g potassium phosphate (monobasic), 8.6 g sodium chloride, 0.1% sodium azide, 1 ml stock green dye, and distilled water added to bring the volume to 1000 mls. The Sample Diluent was then filtered through a 0.2 micron filter.

2. 100 microliters of the Sample Diluent solutions were placed in the designated wells at room temperature for 15 minutes to allow completion of the antigen-antibody binding process. Following incubation, the wells emptied and washed four times with PBS solution.

3. The wells were exposed to a working conjugated antibody solution consisting of 1 part per volume horseradish peroxidase conjugates IgG and IgM specific antibodies, and 3000 part per volume conjugate diluent (Medix) consisting of phosphate buffer, protein stabilizer, and 0.02% thimerosal, to which was added 0.01% by volume a protease inhibitor (commercially available from Miles Pentex).

4. 100 microliter of the working conjugated antibody solution was placed in each microtiter well and allowed to incubate at room temperature for 15 minutes. After incubation, the wells were rinsed four times with PBS solution to remove unbound conjugated antibodies.

5. Each well was assayed for horseradish peroxidase activity by mixing equal volumes (3,3',5,5') Tetramethylbenzidine (Kirkegarrd Perry) and hydrogen peroxide solution and dispersing 100 microliters of this substrate solution into each well. The presence of the anti-dsDNA was detected by a blue color appearing after the 10 minute room temperature incubation. 100 microliters per well of 2.5N sulfuric acid terminated the reaction producing a yellow color. The yellow color was quantitated at 450 nm using a Dynatech MR600 plate reading spectrophotometer.

Detection of anti-dsDNA (IgG & IgM)

| Source | Mean O.D. |
| --- | --- |
| CDC Ref Std. | 1.08 |
| anti DNA pos | 1.13 |
| pos SLE #1 | .54 |
| pos SLE #2 | 1.75 |
| pos anti nucleolar | .10 |
| normal serum | .09 |

EXAMPLE 2

Adsorption of anti-dsDNA from Serum by Uncoated Polystyrene Wells

To demonstrate the beneficial effect of the coating treatment, polystyrene wells were left totally uncoated but exposed to the sera and the standards as described in the previous example. The wells were then exposed to horseradish peroxide conjugated IgG and IgM antibodies, and assayed for peroxidase activity. As expected, only slight selectivity was exhibited by untreated wells and high amounts of non-specific binding led to very high background absorbance.

| Source | AU/ML* | O.D. Coated as in Example 1 | O.D. Uncoated Wells |
|---|---|---|---|
| Calibrator | | | |
| 1 | 120 | 1.38 | 1.28 |
| 2 | 60 | 1.05 | 1.08 |
| 3 | 30 | .55 | .77 |
| 4 | 15 | .37 | .57 |
| 5 | 7.5 | .29 | .67 |
| 6 | 3.8 | .22 | .50 |
| Normal Serum 1 | 8 | .28 | .84 |
| Normal Serum 2 | 9 | .29 | .97 |
| Normal Serum 3 | 3 | .19 | .65 |
| High Positive SLE | | | |
| 1 | 112 | 1.34 | .54 |
| 2 | 50 | .89 | .51 |
| 3 | 120 | 1.96 | 1.67 |
| Low Positive SLE | | | |
| 1 | 13 | .35 | 1.76 |

*AU/ML values calculated in previous experiment.

EXAMPLE 3

A Diagnostic Test Kit Assay Procedure

The kit contains pre-coated microwells and:

1 vial (30 ml) of Sample Diluent (green solution containing 0.1% sodium azide);

6 vials (200 ul each) of Assay Standards for anti-dsDNA, containing these levels of anti-dsDNA activity 120, 60, 30, 15, 7.5, 3.8 AU/ml (anti-dsDNA activity 100 AU/ml of this assay calibrator has an antigen binding capacity of $59 \times 10^{-4}$ ug of DNA);

1 vial of high positive human serum control (about 100 AU/ml);

1 vial of moderate positive human serum control (about 25 AU/ml);

1 vial of negative human serum control (about 3 AU/ml). Also included in the diagnostic kit was a vial (15 ml) of conjugated antibody working solution containing horseradish peroxidase conjugated anti-human IgG, and IgM;

1 bottle (8 ml) of TMB Substrate; solution A containing 3,3',5,5',tetramethylbenzidine;

1 bottle (8 ml) of TMB Substrate; Solution B containing hydrogen peroxide. When mixed with equal parts Solution A will form a substrate capable of generating a colored product;

1 bottle (12 ml) of Stop Reagent containing 2.5N H2SO4 (1N HCL can be substituted);

1 pack of Phosphate Buffered Saline (PBS) which reconstitutes to 2 liters of 0.01M PBS, pH 7.3, which is utilized as a wash solution.

Plate Template

The various reagents of the kit were utilized to perform the assay. The directions for the method of assaying for anti-dsDNA were included in the kit and these directions were followed precisely during this experiment.

The plate templates were labeled for sample placement in the microwells. A 1:50 dilution of the standards, controls and patient samples was prepared in Sample Diluent (green solution). 10 ul of sample was added to 500 ul sample diluent in a one volume to 50 volume sample dilution. 1:50 dilutions of the assay standards and controls were diluted in the same manner.

100 ul of each diluted sample, control or standard was added to the appropriate microwell(s). The wells were allowed to incuate for 15 minutes at room temperature. To perform the rinse step the contents of PBS packet was added to 2 liters of reagent grade water, and the solution was mixed well until all the crystals were dissolved. Then the PBS buffer was used to wash the wells four times. The microwells were inverted between each wash to empty the fluid, after which the wells were drained and blotted on absorbent paper to remove residual wash fluid. Per the kit instructions, the wells were not allowed to dry-out between washes.

100 ul of working conjugated antibody (red solution) was added to each well, incubated for 15 minutes at room temperature, and then the wells were again washed four times with PBS solution.

The working substrate solution was prepared just before use, according to the kit instructions. Equal volumes of TMB Substrate Solution A and TMB Substrate Solution B were combined to form the color generating substrate. The kit instructed that if properly combined this substrate solution would be colorless and it was colorless. Next a 100 ul of the colorless working substrate solution was added to each well and the wells were incubated for ten minutes at room temperature.

Next 100 ul stop reagent was added to each well to end the enzyme reaction, and the O.D. of each well was read at 450 nm against a water blank. A standard curve graph was generated by plotting AU/ml of standards against O.D. of standards, and sample results were obtained from this standard curve.

| Source | O.D. | AU/ml |
|---|---|---|
| Calibrator 1 | 0.2 | 3.8 |
| Calibrator 2 | 0.3 | 7.5 |
| Calibrator 3 | 0.4 | 15 |
| Calibrator 4 | 0.57 | 30 |
| Calibrator 5 | 0.88 | 60 |
| Calibrator 6 | 1.24 | 120 |
| Refer to Graph 2 | | |
| Controls | | |
| high positive | 1.11 | 104 |
| moderate positive | .55 | 24 |
| negative | .14 | 2 |
| normal human sera #1 | .14 | 2 |
| normal human sera #2 | .04 | 1 |
| normal human sera #3 | .18 | 3 |
| SLE positive #1 | .53 | 23 |
| SLE positive #2 | 1.36 | 130 |
| SLE positive #3 | 1.48 | 142 |

EXAMPLE 4

Accelerated Stability Study

DNA coated microwells were treated with S1-nuclease using the optimized protocol, then duplicate microwells were stored at 37 degrees C. and 30 degrees C., and each set of wells was tested at various time intervals using anti-dsDNA and anti-ssDNA monoclonal antibodies. The results of this experiment are shown in the following table:

| Real Time In Days* | Equivalent Time In Months** | % ssDNA Activity |
|---|---|---|
| 0 | 0 | 3-4% |

-continued

| Real Time In Days* | Equivalent Time In Months** | % ssDNA Activity |
|---|---|---|
| 1 | 1.6 | 3-4% |
| 2 | 3.0 | 2-3% |
| 5 | 7.5 | 3-4% |
| 7 | 10.5 | 4-5% |
| 9 | 13.5 | 3-4% |
| 13 | 19.5 | 3-4% |

*incubated at 37 degrees C.
**if incubated at 4 degrees C.

The dsDNA activity in these microwells remained unchanged during the accelerated stability study. The results obtained with the microwells stored at 30 degrees C. were similar to those presented above and confirmed that the stability of the dsDNA coated on the microwells using this protocol was equivalent to more than one year without the generation of significant amounts of ssDNA.

EXAMPLE 5

Accelerated Stability Study on 3 sets of Coated Microwells

I. The microwells used in this experiment were coated by three separate coating methods and are designated as microwells (a), microwells (b), and microwells (c) respectively.

A. the 3 sets of microwells were coated by the following procedures:

(a) the method depicted in example 1 (microwell (a))

(b) the method detailed in the article entitled "An Improved ELISA for Anti-Native DNA by Elimination of Interference by Anti-Histone Antibodies in *Journal of Immunological Methods*, 63 (1983) 359-366 by Rubin et al (Rubin Method (microwell (b)); and (c) the method in the previous article by Rubin et al with a modification that the casein blocker [described in an article entitled "Quantitative Differences Among Various Proteins as Blocking Agents for ELISA Microfilter Plates", in the *Journal of Immunological Methods*, 101 (1987) 43-50 by Vogt et al] was used in place of the gelatin required in Rubin et al, (this method is hereinafter referred to as the "Rubin-Vogt Method") (microwell (c)).

B. To pre-coat the microwells with dsDNA according to Rubin Method, the following procedure was followed:

1. Methylated bovine serum albumin (hereinafter "Rubin mBSA") was dissolved at a ratio of 10 micrograms/ml in water.

2. One milliliter of the Rubin mBSA solution was pipetted into each well of the microtiter plates.

3. After 90 minutes the Rubin mBSA solution was discarded and the wells were washed 3 times with PBS, inverted and allowed to dry.

4. The DNA antigen prior to immobilization was subjected to $S_1$ nuclease treatment according to the "Standard Reaction" described in Vogt, V. M., 1973, Eur., J. Biochem. 33. 192. The DNA was dissolved at 2 mg/ml in 0.01M Tris ph 7.5, it was sonicated and heated for 15 minutes at 100° C. then chilled in ice water.

5. The heat denatured DNA was placed in 0.2 ml of the following buffer 0.03 m sodium acetate, pH 4.6, 0.05 m NaCl, 1 mM $ZnSO_4$, 5% glycerol. Incubation was carried out at 45° C. and terminated by chilling and addition of 0.4 ml ice-cold 10% perchloric acid.

6. The solution was passed through nitrocellulose filters (Sartoriurs Membranfilter GmbH).

7. The following procedure for moving the DNA from the $S_1$ nuclease digestion buffer to PBS was followed:

8. DNA antigen (calf thymus) was diluted in PBS, pH 7.2, (0.14 m NaCl, 0.01 m phosphate buffer) to a concentration of 2.5 micrograms/ml.

(a) After digestion was complete, NaCl was added so that the final concentration of salt would come to 150 mM.

(b) Two volumes of −20° C. absolute ethanol were then added, and the entire mixture stored at −20° C. for two hours.

(c) The DNA was pelleted by centrifuging at 15,000 rpm for 15 minutes. The supernatant was removed and the DNA pellet washed one time with 70% ethanol and allowed to dry.

(d) The DNA was then resuspended in PBS and used for coating microwells.

9. 0.2 ml of the DNA solution was added to each microwell and after incubation the DNA solution was decanted.

10. 0.3 ml of gelatin at 1 mg/ml was incubated for 18 hours and the plates were stored.

11. Just prior to use the immobilized DNA microtiter plates were redigested with $S_1$ nuclease by rinsing and then incubating the wells with 0.25 ml $S_1$ nuclease at 4 U/ml in 0.03M sodium acetate buffer, pH 4.4, containing 0.1M NaCl, 1 mM $ZnCl_2$, 100 micrograms bovine serum albumin (BSA/ml).

12. After 4 hours of shaking at room temperature the wells were rinsed twice with PBS containing 0.05% Tween 20 (PBS-Tween).

C. To pre-coat the microwells with dsDNA according to the Rubin-Vogt Method the procedure listed above as steps B1-12 were followed except instead of step 10, the following step was inserted:

Step 10. Step for Rubin-Vogt Method:

(a) A casein solution was prepared by stirring. About 2 g of purified casein powder in 100 ml water while adding 0.1M NaOH dropwise to maintain a pH of 6.8-7.2. After the pH had stabilized, the suspension was stirred overnight at room temperature, then filtered through standard-grade paper. This saturated casein solution (which remained slight turbid) contained 1.5% protein.

(b) 150 microliters of the casein solution was pipetted into each well and incubated at 37° C. for one hour then washed with deionized water 5 times, and the plates were stored. Then steps B11-B12 were performed as above.

II. Accelerated Stability Study on Microwells (a), (b), and (c).

1. Microwells (a), (b), and (c) were placed in storage at 37° C. for seven days which is approximately equivalent to ten months—one year of storage at 4° C.

2. Each day the behavior of two well characterized sera a negative control serum, known to be free of anti-dsDNA antibodies, and a positive control serum (100 AW/ml) containing elevated levels of anti dsDNA antibodies was monitored.

3. Prior to assaying the sera on the microwells (b) and (c) the $S_1$ nuclease treatment outlined in this example in steps B11-B12 was performed.

4. The negative and positive sera each were diluted with sample diluent in a 1:50 ratio; 1 part serum to 50 parts sample diluent.

5. 100 microliters of the sample diluent solutions and 100 microliters of a reagent blank containing no human serum were pipette into separate wells at room temperature for 15 minutes. After incubation the well were emptied and washed 4 times with PBS solution.

6. 100 microliters of the working conjugated antibody solution was placed in each well and incubated at room temperature for 15 minutes, then rinsed 4 times with PBS.

7. Each well was assayed for horseradish peroxidase activity by mixing equal volumes (3,3',5,5') Tetramethylbenzidine (Kirkegaard Perry) and hydrogen peroxide solution and dispensing 100 microliters of this substrate solution into each well. The presence of the anti-dsDNA was detected by a blue color appearing after the 10 minute room temperature incubation. 100 microliters per well of 2.5N sulfuric acid terminated the reaction producing a yellow color. The yellow color was quantitated at 450 nm using a Dynatech MR600 plate reading spectrophotometer.

The results of the accelerated stability studies are shown on FIG. 3 showing the microwells (a) made and assayed in accordance with the present invention. FIG. 4 showing microwells (b) made in accordance with the Rubin method. FIG. 5 made in accordance with the Rubin-Vogt method.

III. Discussion of Accelerated Stability Results

The absorbance values obtained from these sera should remain fairly stable. An increase in the absorbance value of the negative control indicates an increase in nonspecific binding. A decrease in absorbance values of the positive control indicates that the antigen has in some way changed so that it is not recognized by the antibodies. The ratio of positive to negative O.D. values is also a useful indicator of how well the assay is able to distinguish between positive and negative samples. This ratio should be rather large, generally at least a factor of five.

Turning to the FIG. 3:

The absorbance of the reagent blank is negligible, as expected. The absorbance of the negative control serum is stable and only slightly higher than the absorbance of the reagent blank, which demonstrates that the kit is very specific and not reacting with antibodies found in normal sera. The absorbence of the positive control does vary slightly over time, but it remains well above the negative control absorbance throughout the study. The positive/negative ratio is greater than 8.5 throughout the study. There is no appearance of degradation.

Turning to FIG. 4 showing microwell b:

The microwells coated according to Rubin has less satisfactory performance and stability. From the beginning of the study, the absorbance of the negative control serum is quite high, indicating that these microwells cross-react with many antibodies found in human serum. The positive controls absorbance/negative controls absorbance ratio is only 1.6 at Day 0 of the study and decreases at later days. On Days 5 and 7, the positive control serum actually had a lower value than the negative control serum. The high absorbance of the reagent blank on these days indicates that virtually all the binding is nonspecific. Deterioration of the kit is apparent by Day 3, which is equivalent to approximately 4.5 months of storage at refrigerated temperatures.

Turning to FIG. 5 showing microwell c:

The kit made with microwells coated according to the Rubin-Vogt method also had less then satisfactory performance. In this microwell (c), the absorbance of the negative control serum is very high throughout the study, indicating a high level of cross-reactivity. The tendency of the negative control absorbance to rise starting at Day 5 indicates that the kit may be degenerating, causing an increase in cross reactivity. The positive/negative ratio ranges from only 1.2 to 1.6. This kit appears to be somewhat more stable than the kit produces with Rubin method microwells, but the results are unacceptable throughout the study.

EXAMPLE 6

Clinical Specificity of Microwells (a), (b), and (c)

The microwells (a), (b), and (c) made according to example 5 with the assay performed in accordance with the present invention were tested for clinical specificity using 33 samples from normal blood donors, who should be negative for anti-dsDNA antibodies, and 36 serum samples from patients with systemic lupus erythematosus (SLE), some of whom should be positive for anti-dsDNA antibodies. The normal cut-off of the assay has been set at 26 AU/ml, determined as the mean plus two standard deviations of 150 serum samples from normal blood donors. The results are given in the tables below.

TABLE 1

| Sample | Normal Sample Values | | |
|---|---|---|---|
| | Present Invention | Rubin | Rubin-Vogt |
| NS1 | 17.1 | 28.9 | 41.6 |
| NS2 | 10.7 | 16.8 | 32.6 |
| NS3 | 9.6 | 17.6 | 30.4 |
| NS4 | 16.3 | 16.3 | 21.6 |
| NS5 | 18.4 | 40.7 | 40.5 |
| NS6 | 14.4 | 21.2 | 29.2 |
| NS7 | 8.5 | 28.2 | 30.1 |
| NS9 | 20.3 | 15.7 | 29.4 |
| NS10 | 20.3 | 14.6 | 15.8 |
| NS11 | 16.0 | 17.8 | 27.4 |
| NS12 | 17.5 | 10.5 | 15.5 |
| NS13 | 16.0 | 13.9 | 22.4 |
| NS14 | 16.3 | 71.4 | 23.7 |
| NS15 | 18.7 | 18.7 | 32.2 |
| NS16 | 27.8 | 18.0 | 23.8 |
| NS17 | 18.7 | 17.3 | 23.7 |
| NS18 | n.d. | 30.1 | 22.2 |
| NS19 | 21.4 | 12.5 | 20.0 |
| NS20 | 11.2 | 32.0 | 20.8 |
| NS21 | 21.6 | 29.2 | 34.9 |
| NS22 | 16.6 | 23.6 | 36.8 |
| NS23 | 14.4 | 6.0 | 10.3 |
| NS24 | 18.2 | 5.4 | 12.2 |
| NS25 | 14.4 | 19.0 | 22.5 |
| NS26 | 17.0 | 24.7 | 12.5 |
| NS27 | 14.0 | 22.7 | 12.8 |
| NS28 | 24.2 | 45.6 | 22.9 |
| NS29 | 14.0 | 54.5 | 29.8 |
| NS30 | 32.8 | 9.9 | 32.8 |
| NS32 | 10.9 | 19.2 | 14.6 |
| NS41 | 23.1 | 29.9 | 30.7 |
| NS35 | 20.1 | 72.7 | 19.3 |
| NS36 | 16.5 | 50.4 | 26.7 |
| NS38 | 21.8 | 79.9 | 18.7 |
| NS39 | n.d. | 52.4 | 19.0 |
| NS40 | 17.2 | 35.6 | 15.8 |
| specificity: | 94% | 58% | 61% |

TABLE 2

| Sample | SLE Patient Sample Values | | |
|---|---|---|---|
| | Present Invention | Rubin | Rubin Vogt |
| Mil1 | 16.9 | 40.7 | 30.2 |
| Mil3 | 20.1 | 16.7 | 22.6 |

TABLE 2-continued

| Sample | SLE Patient Sample Values | | |
|---|---|---|---|
| | Present Invention | Rubin | Rubin Vogt |
| Mil4 | 11.3 | 29.6 | 26.8 |
| Mil5 | 13.7 | 45.2 | 35.7 |
| Mil6 | 58.5 | 16.6 | 29.2 |
| Mil7 | 87.4 | 16.4 | 27.3 |
| Mil8 | 60.2 | 15.4 | 30.7 |
| Mil9 | 24.0 | 67.3 | 61.5 |
| Mil10 | 15.1 | 18.7 | 17.7 |
| Mil11 | 19.7 | 33.5 | 13.7 |
| Mil12 | 8.8 | 7.7 | 9.7 |
| Mil13 | 14.1 | 27.5 | 17.4 |
| PDS3 | 50.7 | 117 | 41.8 |
| PDS8 | 28.8 | 17.8 | 25.6 |
| PDS22 | 96.4 | 49.9 | 40.6 |
| Mil14 | 20.1 | 50.1 | 19.9 |
| Mil15 | 38.8 | 35.5 | 35.1 |
| Mil18 | 18.3 | 46.6 | 41.1 |
| Mil19 | 58.8 | 32.3 | 41.8 |
| Mil21 | 140 | 80.0 | 47.9 |
| Mil22 | 8.8 | 78.1 | 59.1 |
| Mil23 | 3.2 | 39.6 | 47.6 |
| Mil24 | 13.7 | 58.2 | 46.3 |
| Mil25 | 26.4 | 19.2 | 13.4 |
| Mil26 | 8.8 | 32.5 | 41.5 |
| Mil27 | 15.5 | 23.3 | 29.5 |
| Mil28 | 17.6 | 29.4 | 36.8 |
| Mil29 | 31.7 | 55.1 | 38.4 |
| Mil30 | 10.9 | 41.9 | 22.5 |
| Mil31 | 7.8 | 26.8 | 40.2 |
| Mil41 | 26.4 | 14.5 | 18.6 |
| Mil33 | 12.0 | 65.0 | 29.7 |
| Mil34 | 52.8 | 30.2 | 16.8 |
| Mil35 | 19.7 | 19.3 | 19.4 |
| Mil36 | 27.1 | 91.4 | 55.6 |
| Mil38 | 6.7 | 61.3 | 43.9 |
| Mil40 | 15.5 | 22.5 | 19.5 |
| Mil42 | 32.0 | 45.8 | 13.0 |

II. Discussion of results

The present invention was 94% specific, the microwells (b) were only 58% specific and the microwells (c) were only 61% specific. Clearly the high levels of cross-reactivity observed in the results of experiment 5 have detrimentally affected the clinical specificity of the microwells (b) and (c).

EXPERIMENT 7

Sensitivity

Three sets of microwells made according to example 5 and using the assay protocol for the present invention were tested for clinical sensitivity using 33 samples from normal blood donors, who should be negative for anti-dsDNA antibodies, and 36 serum samples from patients with systemic lupus erythematosus (SLE), some of whom should be positive for anti-dsDNA antibodies. The results are given in the tables above.

II. Discussion of Results

The true sensitivity of these tests is how many samples from diseased individuals have values that are significantly higher than the values of samples from normal individuals. Therefore the cut-off values of the kits based on the Rubin and Rubin-Vogt methods was based on the mean plus two standard deviations of the 33 samples from normal individuals tested in these kits. The revised cut-off values are higher than the cut-off of the present invention kit. The cut-off of the kits with Rubin microwells was determined to be 66 AU/ml, and the cut-off of the kits with the Rubin-Vogt microwells was found to be 40.4 AU/ml. Using the revises cut-off values, only 5 (13%) of samples were detected as positive according to the kit using the Rubin microwells, and 13 (33%) of SLE samples were detected as positive according to the kit using Rubin-Vogt microwells. The sensitivity of the present invention for this group of specimens was at least 36%.

The foregoing examples serve to illustrate the efficiency and utility of the methylated BSA to provide a coating which inhibits non-specific binding and provides a coating capable of affixing dsDNA antigen evenly over the solid support. Without being bound to the specific quantities given in the definitional section, it is possible to utilize a wide latitude of concentrations of mBSA or other similar, functionally equivalent substitutes which have the capability to evenly attach dsDNA antigen to the support solid by providing a charged surface or by any other like mechanism to affix the dsDNA and to continue to inhibit non-specific binding.

Likewise, the blocker utilized in the preferred embodiment of this invention to stabilize the shelf life and eliminate non-specific binding cannot be limited to the compounds or the ingredients or the concentrations thereof listed in the definitional section. A variety of functional equivalent blocking agents are known to those skilled in the art. A partial listing of some materials which could be utilized to perform a similar function is found in (Robert F. Bogt; J. Immunological Methods, 101, 43–50 [1987]) and is hereby incorporated herein by reference. A third element which plays a function in eliminating non-specific binding is the $S_1$ nuclease used to degrade the ssDNA and thus to avoid any cross reactivity between the anti-dsDNA and the undesired ssDNA. The described method of limiting cross reactivity is not limited to the definition given but the method can be performed with varying concentrations of $S_1$ nuclease or other similar, endonuclease enzymes, or similar functional equivalents which are capable of eliminating ssDNA without adversely affecting the dsDNA present in the invention.

The treatment of the solid support which can be any of a variety of formats, i.e. test tubes, plates, wells, etc., made of various suitable materials, i.e. glass, plastics, etc. with the aforementioned technology affords many important and useful approaches to the detection of the anti-dsDNA antibodies. The detection of anti-dsDNA need not be limited to the conjugation of enzymes. Addition of fluorescent chemicals such as fluorescence or the like to the antibody will impart fluorescence to the assay if the antibody is present. Similarly, conjugation of the antibody with a radionuclide will impart radioactivity to the assay if the antibodies are present in the assay. Many other methods of detection of antibodies also exist, and these methods will yield positive results provided that the antibody exists in the assayed sera and is affixed according to the methods described herein.

The test kit and the underlying coating and detection methods herebefore described are not intended to be limited by the assay format described or by the volumes or the concentrations or specific ingredients given for the various reagents, controls, and calibrators. It should be understood that similar chemical equivalents or other functional equivalents of the components found in the coatings, or in any of the various reagents, controls, and calibrators can be utilized within the scope of this invention.

It is contemplated that the inventive concepts herein described may have differing embodiments and it is intended that the appended claims be construed to include all such alternative embodiments of the invention except insofar as they are limited by the prior art.

We claim:

1. A diagnostic element adapted to detect the presence of anti-dsDNA antibodies in a sample specimen upon contact with said sample specimen, comprising:
   a support member, selected from the group consisting of plates, test tubes, and wells;
   a coating on a surface portion of said support member, said first coating consisting essentially of methylated bovine serum albumin as a constituent thereof whereby said methylated bovine serum albumin provides immobilization sites;
   dsDNA antigens specific for said anti-dsDNA antibodies, said dsDNA antigens being immobilized on said coating at occupied ones of said immobilization sites; and
   a blocking layer disposed on said coating, said blocking layer consisting essentially of a blocking material operative to block a majority of said immobilization sites other than the occupied ones thereof whereby said blocking layer provides a contact surface available to be contacted by said sample specimen with said contact surface having dsDNA antigens forming binding sites specific for said anti-dsDNA antibodies while being substantially free of ssDNA antigens forming binding sites; wherein said blocking layer is operative to stabilize said dsDNA antigens immobilized on the occupied ones of said immobilization sites; and wherein said contact surface has a specificity greater than sixty-two percent.

2. A diagnostic element in accordance with claim 1 wherein said blocking material includes casein.

3. A diagnostic element in accordance with claim 2 wherein said blocking material includes glycerol and sucrose.

4. A diagnostic element in accordance with claim 1 wherein said contact surface has a specificity greater than ninety percent.

5. A test kit for detecting the presence of anti-dsDNA specific antibodies in a sample specimen, comprising:
   (a) a diagnostic element including a support member, selected from the group consisting of plates, test tubes and wells having a coating consisting essentially of methylated bovine serum albumin that provides immobilization sites, dsDNA antigens attached at occupied ones of said immobilization sites, said dsDNA antigens specific for said anti-dsDNA antibodies, and a blocking layer consisting essentially of a blocking material operative to block a majority of said immobilization sites other than the occupied ones thereof, said diagnostic element thereby providing a contact surface having dsDNA antigens forming binding sites specific for said anti-dsDNA specific antibodies whereby said anti-dsDNA specific antibodies may be bound to said diagnostic element;
   (b) a sample diluent for use in diluting said sample specimen prior to application thereof to said contact surface;
   (c) a conjugated antibody solution including anti-human IgM and IgG antibodies conjugated to a label and operative to affix to bound ones of said anti-dsDNA specific antibodies upon contact therewith such that the relative amount of anti-dsDNA specific antibodies in said sample specimens can be determined;
   (d) a label identifying solution operative to permit analyzation of attached conjugated antibody solution labels.

6. A diagnostic test kit in accordance with claim 5 wherein said sample diluent includes bovine serum which is operative to inhibit the binding of non-specific antibodies to said coating.

7. A method of producing a diagnostic element adapted to detect the presence of anti-dsDNA antibodies in a sample specimen, comprising the steps of:
   providing a support selected from the group consisting of plates, test tubes, and wells;
   coating a surface portion of said support with a first substance consisting essentially of methylated bovine serum albumin to form a layer having immobilization sites;
   contacting said layer with dsDNA antigens specific for anti-dsDNA antibodies whereby at least some of said dsDNA antigens attach to said methylated bovine serum albumin at some of said immobilization sites;
   washing said first layer after attachment of said dsDNA antigens with a second substance including an enzyme capable of digesting ssDNA; and
   coating said first layer with a third substance consisting essentially of a blocking material operative to eliminate available ones of said immobilization sites and to stabilize said dsDNA antigens at a contact surface;
   wherein said contact surface has a specificity greater than sixty-two percent.

8. The method according to claim 7 wherein said second substance includes an $S_1$ nuclease digestion buffer operative to eliminate ssDNA.

9. The method according to claim 7 wherein the step of contacting said first layer with dsDNA antigens and the step of coating said first layer with a third substance produces a ratio of specific to non-specific binding sites such that the amount of specific binding produced by contact of said contact surface with a positive control to the amount of non-specific binding produced by contact of said contact surface with a negative control is at least 1.7 to 1.

10. The method according to claim 9 wherein said ratio is at least 5 to 1.

11. The method according to claim 7 wherein said contact surface has a specificity greater than ninety percent.

12. A method for detecting the presence of anti-dsDNA antibody in a sample specimen comprising the steps of:
    (a) providing a diagnostic element in the form of a support member, selected from the group consisting of plates, test tubes, and wells having a coating comprising consisting essentially of methylated bovine serum albumin that provides immobilization sites, dsDNA antigens attached at occupied ones of said immobilization sites, said dsDNA antigens specific for said anti-dsDNA antibodies, and a blocking layer consisting essentially of a blocking material operative to block a majority of said immobilization sites other than the occupied ones thereof, said diagnostic element thereby providing a contact surface having dsDNA antigens forming binding sites specific for said anti-dsDNA specific antibodies whereby said anti-dsDNA specific antibodies may be bound to said diagnostic element;

(b) contacting said contact surface with said sample specimen to be tested for the presence therein of said anti-dsDNA antibody;

(c) within 15 minutes after step (b), contacting said contact surface with a labeled antibody whereby at least some of said labeled antibody binds to said anti-dsDNA antibody;

(d) rinsing the contact surface after contact thereof with said labeled antibody; and (e) measuring the amount of said bound label within 105 minutes after contact of said contact surface with said sample specimen whereby an amount of anti-dsDNA antibody may be determined.

13. A method in accordance with claim 12 wherein the step of measuring the amount of said bound label is done within 45 minutes after contact of said contact surface with said sample specimen.

* * * * *